United States Patent
Vaez-Iravani et al.

(10) Patent No.: US 7,623,229 B1
(45) Date of Patent: Nov. 24, 2009

(54) SYSTEMS AND METHODS FOR INSPECTING WAFERS

(75) Inventors: Mehdi Vaez-Iravani, Los Gatos, CA (US); Stephen Biellak, Sunnyvale, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 12/246,622

(22) Filed: Oct. 7, 2008

(51) Int. Cl.
*G01N 21/88* (2006.01)
(52) U.S. Cl. .................. 356/237.5; 356/237.4; 356/394
(58) Field of Classification Search ... 356/237.1–237.6, 356/394, 239.3, 239.7, 239.8; 250/559.04, 250/559.16, 559.41
See application file for complete search history.

(56) References Cited

U.S. PATENT DOCUMENTS

| | | | |
|---|---|---|---|
| 5,798,829 A | 8/1998 | Vaez-Iravani et al. | |
| 6,034,776 A * | 3/2000 | Germer et al. | 356/369 |
| 6,201,601 B1 | 3/2001 | Vaez-Iravani et al. | |
| 6,271,916 B1 | 8/2001 | Marxer et al. | |
| 6,384,910 B2 | 5/2002 | Vaez-Iravani et al. | |
| 6,538,730 B2 * | 3/2003 | Vaez-Iravani et al. | 356/237.2 |
| 6,590,645 B1 | 7/2003 | Chen et al. | |
| 6,606,153 B2 | 8/2003 | Marxer et al. | |
| 6,618,134 B2 | 9/2003 | Vaez-Iravani et al. | |
| 6,639,662 B2 | 10/2003 | Vaez-Iravani et al. | |
| 6,657,715 B2 | 12/2003 | Vaez-Iravani et al. | |
| 6,862,096 B2 | 3/2005 | Vaez-Iravani et al. | |
| 6,888,627 B2 * | 5/2005 | Leslie et al. | 356/237.2 |
| 6,891,611 B1 | 5/2005 | Vaez-Iravani et al. | |
| 6,956,644 B2 | 10/2005 | Biellak et al. | |
| 6,999,183 B2 | 2/2006 | Nielson et al. | |
| 7,002,677 B2 | 2/2006 | Bevis et al. | |
| 7,016,031 B2 | 3/2006 | Chen et al. | |
| 7,038,772 B2 | 5/2006 | Chen et al. | |
| 7,038,773 B2 | 5/2006 | Kuhlmann et al. | |
| 7,061,598 B1 | 6/2006 | Bevis et al. | |
| 7,064,821 B2 | 6/2006 | Vaez-Iravani et al. | |
| 7,068,363 B2 | 6/2006 | Bevis et al. | |
| 7,079,238 B2 | 7/2006 | Vaez-Iravani et al. | |
| 7,102,744 B2 | 9/2006 | Marxer et al. | |
| 7,106,432 B1 | 9/2006 | Mapoles et al. | |
| 7,110,106 B2 * | 9/2006 | Xu et al. | 356/237.5 |
| 7,116,413 B2 | 10/2006 | Vaez-Iravani et al. | |
| 7,119,897 B2 | 10/2006 | Vaez-Iravani et al. | |
| 7,130,036 B1 | 10/2006 | Kuhlmann et al. | |

(Continued)

OTHER PUBLICATIONS

U.S. Appl. No. 60/974,030 (Bhaskar et al.) entitled Systems and Methods for Creating Persistent Data for a Wafer and for Using Persistent Data for Inspection-Related Functions filed on Sep. 20, 2007.

(Continued)

*Primary Examiner*—Sang Nguyen
(74) *Attorney, Agent, or Firm*—Ann Marie Mewherter

(57) ABSTRACT

Systems and methods for inspecting wafers are provided. One system includes a detection subsystem configured to separately and simultaneously detect light scattered from different portions of a single spot obliquely, or normally, illuminated on a wafer and to separately generate output responsive to the separately detected light that can be used to detect defects on the wafer. The system can, therefore, effectively perform a multi-spot type of inspection of the wafer using only a single obliquely or normally illuminated spot on the wafer.

21 Claims, 4 Drawing Sheets

U.S. PATENT DOCUMENTS

| | | | |
|---|---|---|---|
| 7,130,039 B2 * | 10/2006 | Vaez-Iravani et al. | 356/237.5 |
| 7,184,138 B1 | 2/2007 | Li | |
| 7,199,874 B2 | 4/2007 | Bevis et al. | |
| 7,206,066 B2 | 4/2007 | Vurens et al. | |
| 7,218,392 B2 | 5/2007 | Biellak et al. | |
| 7,218,768 B2 | 5/2007 | Evans et al. | |
| 7,271,921 B2 | 9/2007 | Shortt | |
| 7,304,310 B1 | 12/2007 | Shortt et al. | |
| 7,345,754 B1 | 3/2008 | Zhao et al. | |
| 7,417,721 B2 * | 8/2008 | Uto et al. | 356/237.2 |
| 2004/0057045 A1 | 3/2004 | Vaez-Iravani et al. | |
| 2005/0018181 A1 | 1/2005 | Vaez-Iravani et al. | |
| 2005/0206886 A1 | 9/2005 | Vaez-Iravani et al. | |
| 2006/0092427 A1 | 5/2006 | Nielsen et al. | |
| 2006/0109457 A1 | 5/2006 | Miller et al. | |
| 2006/0274304 A1 | 12/2006 | Haller et al. | |
| 2006/0285112 A1 | 12/2006 | Reich et al. | |
| 2007/0081151 A1 | 4/2007 | Shortt et al. | |
| 2007/0103676 A1 | 5/2007 | Marxer et al. | |
| 2007/0132987 A1 | 6/2007 | Haller et al. | |
| 2007/0229809 A1 | 10/2007 | Belyaev et al. | |
| 2008/0013083 A1 | 1/2008 | Kirk et al. | |
| 2008/0018887 A1 | 1/2008 | Chen et al. | |

OTHER PUBLICATIONS

U.S. Appl. No. 11/110,383 (Shortt et al.) entitled Systems and Methods for Inspecting Specimens Including Specimens That Have a Substantially Rough Uppermost Layer filed on Apr. 20, 2005.

U.S. Appl. No. 11/745,127 (Shortt et al.) entitled Calibration Standards for Inspection Systems, Methods for Forming Calibration Standards for Inspection Systems, and Methods for Calibrating an Inspection System filed on May 7, 2007.

\* cited by examiner

SYSTEMS AND METHODS FOR INSPECTING WAFERS

BACKGROUND OF THE INVENTION

1. Field of the Invention

This invention generally relates to systems and methods for inspecting wafers. Certain embodiments relate to a system that includes a detection subsystem configured to separately and simultaneously detect light scattered from different portions of a single TO spot obliquely illuminated on a wafer and to separately generate output responsive to the separately detected light that can be used to detect defects on the wafer.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices. Accordingly, much work has been done in the field of wafer inspection to increase the sensitivity of inspection systems to smaller and smaller defects.

However, in some cases, unpatterned wafer inspection has reached a limitation in sensitivity, both on ultra smooth surfaces and on rough surfaces. For example, as defect sizes decrease, the difficulty of detecting relatively small defects on relatively rough wafer surfaces increases. Previously, the scattering of light from relatively rough surfaces did not substantially limit inspection system performance since the defects being detected were relatively large. However, as the size of defects decreases, the amount of light scattered from the defects also decreases. As such, the amount of light scattered from defects of relatively small size may be much closer to the amount of light scattered from relatively rough surfaces thereby reducing the sensitivity of many systems for inspection of such surfaces. Therefore, although many currently available inspection systems are capable of detecting relatively large defects on relatively rough surfaces and/or relatively small defects on relatively smooth surfaces, there is still a need for an inspection system that can detect relatively small defects on relatively rough surfaces as well as even smaller defects on relatively smooth surfaces.

Many inspection systems such as those described above are configured to image a single spot or line on the wafer at normal and/or oblique angles of incidence using spherical and/or cylindrical lenses. The single spot or line imaging of these systems also contributes, at least in part, to the relatively low sensitivity (e.g., relatively low signal-to-noise ratio, SNR) of the systems when inspecting certain surfaces. In particular, since a single spot or line on the wafer plane is relatively large (particularly in comparison to the size of the defects typically being detected), the light scattered from the illuminated spot or line will contain a relatively large amount of scattering from the surface of the wafer. Such scattering may be relatively low for relatively smooth surfaces. However, the scattered light from relatively rough wafer surfaces may be much higher and will, therefore, adversely affect the sensitivity of the inspection system.

One way to increase the SNR for relatively rough surface inspection is to decrease the size of the spot on the wafer. However, decreasing the size of the optical spot on the wafer often undesirably decreases the throughput of the inspection system.

Accordingly, it would be advantageous to develop systems and methods for inspecting wafers with enhanced sensitivity for detecting relatively small defects on both smooth and rough surfaces while maintaining a relatively high throughput.

SUMMARY OF THE INVENTION

The following description of various system and method embodiments is not to be construed in any way as limiting the subject matter of the appended claims.

One embodiment relates to a system configured to inspect a wafer. The system includes an illumination subsystem configured to direct light to a spot on the wafer at an oblique angle of incidence. The system also includes a first detection subsystem configured to detect light scattered from one portion of the spot on the wafer and to generate output responsive to the detected light. In addition, the system includes a second detection subsystem configured to separately and simultaneously detect light scattered from different portions of the spot on the wafer and to separately generate different output responsive to the separately detected light. The entire collection space of the second detection subsystem spans only a portion of azimuthal angles at which the first detection subsystem detects the scattered light. The system further includes a computer subsystem configured to detect defects on the wafer using the output generated by the first detection subsystem and the different output separately generated by the second detection subsystem.

In one embodiment, the one portion of the spot has an area on the wafer that is approximately equal to the entire area of the spot on the wafer. In another embodiment, an area of the one portion of the spot is larger than an area of each of the different portions of the spot. In an additional embodiment, none of the different portions within the spot overlap any other of the different portions within the spot. In a further embodiment, the different portions in combination extend across an area within the spot that is smaller than the entire area of the spot.

In one embodiment, the first detection subsystem includes an ellipsoidal collector configured to collect the light scattered from the one portion of the spot on the wafer. In another embodiment, the second detection subsystem is configured to detect the light scattered from the different portions at one or more polar angles that are closer to the wafer than polar angles at which the first detection subsystem detects the scattered light.

In one embodiment, the second detection subsystem is configured to preserve information about the different portion of the spot from which the separately detected light was scattered and to not preserve information about polar and azimuthal angles within the entire collection space of the second detection subsystem at which the light was scattered from the different portions of the spot. In another embodiment, the second detection subsystem includes a collector configured to collect the light scattered from the different portions of the spot.

In one embodiment, the second detection subsystem includes a detector configured to separately and simultaneously detect the light scattered from the different portions of the spot. In one such embodiment, the detector includes a multi-anode photomultiplier tube. In another such embodiment, the detector includes physically separated detection elements, and the second detection subsystem includes a mask positioned in front of the detector to increase optical separation between the physically separated detection elements.

In one embodiment, the second detection subsystem includes a collector configured to collect the light scattered from the different portions of the spot, a first detector configured to separately and simultaneously detect the collected light scattered from the different portions of the spot, and a second detector configured to separately and simultaneously detect the collected light scattered from the different portions of the spot. In another embodiment, the second detection subsystem includes a first detector configured to separately and simultaneously detect the light scattered from the different portions of the spot and a second detector configured to separately and simultaneously detect the light scattered from the different portions of the spot, and the first and second detectors are positioned such that there is a half pixel shift between the first and second detectors. In an additional embodiment, the second detection subsystem includes optical fibers configured to separately and simultaneously direct the light scattered from the different portions to different detection elements such that the different detection elements separately and simultaneously detect the light scattered from the different portions of the spot. In one such embodiment, the second detection subsystem includes micro-lenses positioned in front of the optical fibers and configured to eliminate dead spaces between adjacent optical fibers.

In one embodiment, the second detection subsystem is configured such that the different output separately generated by the second detection subsystem is substantially unaffected by movement of the wafer in a direction substantially perpendicular to a surface of the wafer being inspected. In another embodiment, the illumination subsystem is configured to direct the light to the spot on the wafer at the oblique angle of incidence and a first azimuthal angle, and the second detection subsystem is configured to separately and simultaneously detect the light scattered from the different portions of the spot at one or more azimuthal angles different than the first azimuthal angle. In one such embodiment, the first azimuthal angle and the one or more azimuthal angles are not opposite to each other.

In one embodiment the system includes a third detection subsystem configured to separately and simultaneously detect light scattered from the different portions of the spot on the wafer and to separately generate different output responsive to the scattered light separately detected by the third detection subsystem. In one such embodiment, the second and third detection subsystems collect and detect the scattered light at different azimuthal angles. In another such embodiment, the third detection subsystem includes a refractive collector positioned such that an optical axis of the refractive collector is substantially perpendicular to a surface of the wafer being inspected.

In some embodiments, the system includes a third detection subsystem configured to detect light scattered from the one portion of the spot on the wafer and to generate output responsive to the scattered light detected by the third detection subsystem. In one such embodiment, the third detection subsystem includes a refractive collector positioned such that an optical axis of the refractive collector is substantially perpendicular to a surface of the wafer being inspected.

In one embodiment, the computer subsystem is configured to perform a convolution on the different output separately generated by the second detection subsystem and to detect the defects on the wafer using results of the convolution.

In some embodiments, the system includes a stage configured to rotate and translate the wafer while the light is directed to the spot on the wafer by the illumination subsystem such that the light directed to the spot is scanned across the wafer.

Each of the embodiments of the system described above may be further configured as described herein.

Another embodiment relates to a method for inspecting a wafer. The method includes directing light to a spot on the wafer at an oblique angle of incidence. The method also includes detecting light scattered from one portion of the spot on the wafer and generating first output responsive to the detected light scattered from the one portion. In addition, the method includes separately and simultaneously detecting light scattered from different portions of the spot on the wafer and separately generating different output responsive to the separately detected light. The light scattered from the different portions is detected at only a portion of the azimuthal angles at which the light scattered from the one portion is detected. The method further includes detecting defects on the wafer using the first output and the separately generated different output.

Each of the steps of the method described above may be further performed as described herein. In addition, the method described above may include any other step(s) of any other method(s) described herein. Furthermore, the method described above may be performed by any of the systems described herein.

An additional embodiment relates to a system configured to inspect a wafer. The system includes an illumination subsystem configured to direct light to a spot on the wafer at a substantially normal angle of incidence. The system also includes a first detection subsystem configured to detect light scattered from one portion of the spot on the wafer and to generate output responsive to the detected light. In addition, the system includes a second detection subsystem configured to separately and simultaneously detect light scattered from different portions of the spot on the wafer and to separately generate different output responsive to the separately detected light. The entire collection space of the second detection subsystem spans only a portion of azimuthal angles at which the first detection subsystem detects the scattered light. The system further includes a computer subsystem configured to detect defects on the wafer using the output generated by the first detection subsystem and the different output separately generated by the second detection subsystem. The system embodiment described above may be further configured as described herein.

BRIEF DESCRIPTION OF THE DRAWINGS

Other objects and advantages of the invention will become apparent upon reading the following detailed description and upon reference to the accompanying drawings in which.

Figure 1:
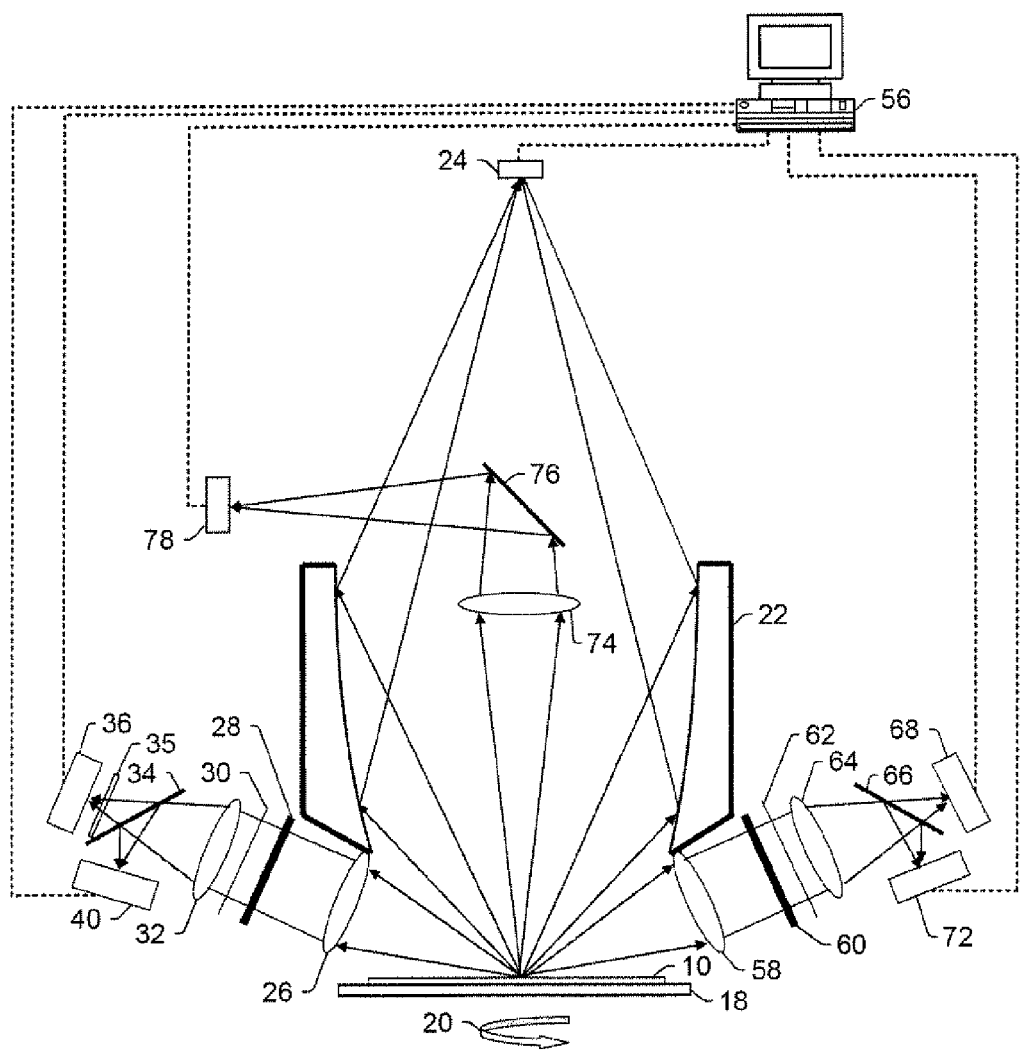
FIG. 1 is a schematic diagram illustrating a side view of one embodiment of a system configured to inspect a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. In this manner, the wafer may be a patterned or an unpatterned wafer. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

The terms "first," "second," and "third" are used herein to differentiate between different detection subsystems, different detectors, etc. The terms "first," "second," and "third" are not used to indicate temporal, spatial, or preferential characteristics of the detection subsystems, detectors, etc.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 2:
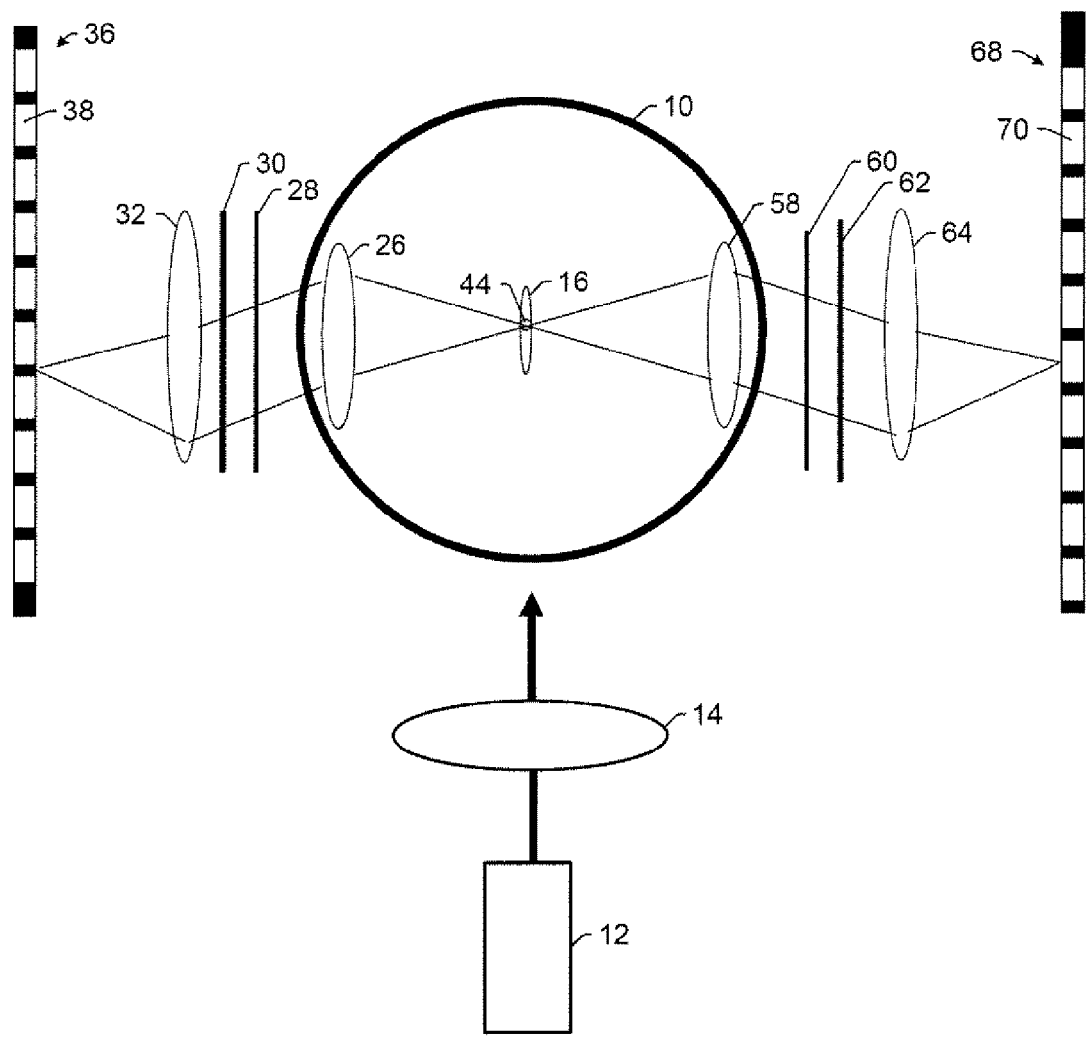
FIG. 2 is a schematic diagram illustrating a plan view of a portion of the system of FIG. 1.

FIGS. 1-2 illustrate one embodiment of a system configured to inspect a wafer. The system includes an illumination subsystem configured to direct light to a spot on wafer 10 at an oblique angle of incidence. For example, the illumination subsystem includes light source 12 shown in FIG. 2. Light source 12 may include any suitable light source such as a laser, a cw laser, or a pulsed laser. Light source 12 may be configured to generate light at any suitable wavelength(s) (e.g., about 355 nm or about 266 nm). The light directed to the wafer may have multiple wavelengths. The multiple wavelengths of light may include multiple, discrete wavelengths of light (e.g., from a polychromatic light source) or a continuous spectrum of wavelengths of light (e.g., from a broadband light source). The multiple wavelengths of light may be directed to the wafer at substantially the same time. Not all of the wavelengths of light generated by the light source may be directed to the wafer (e.g., by use of one or more filters positioned in the path of the light from the light source).

As shown in FIG. 2, the illumination subsystem may include refractive optical element 14 configured to focus the light from light source 12 to spot 16 on wafer 10. Refractive optical element 14 may include any suitable refractive optical element. In addition, refractive optical element 14 may be replaced with two or more refractive optical elements and/or one or more reflective optical elements, which may include any suitable refractive and/or reflective optical element(s) arranged in any suitable configuration. For example, such refractive optical element(s) may include, but are not limited to, a tube lens, a relay lens, a collimating lens, a focusing lens, a condenser lens, or some combination thereof. The illumination subsystem may also include any other suitable optical elements (not shown in FIGS. 1-2) configured to direct and/or focus the light from light source 12 to wafer 10. For example, the illumination subsystem may include a number of optical elements positioned in the path of the light such as folding mirror(s), beam splitter(s), polarizer(s), filter(s), and lenses.

The illumination subsystem may be configured to direct the light from light source 12 to wafer 10 at any suitable oblique angle of incidence. The oblique angle of incidence may vary depending on, for example, the characteristics of the light and the characteristics of the wafer. One suitable oblique angle of incidence may be about 70° from normal to the upper surface of the wafer. In an alternative embodiment, the illumination subsystem may be configured to direct the light from the light source to the spot on the wafer at a substantially normal angle of incidence. In this manner, the illumination subsystem may be configured for normal (or substantially normal) illumination.

The illumination subsystem may also be configured to direct the light to the spot on the wafer at multiple angles of incidence. For example, the illumination subsystem may include an additional light source (not shown in FIGS. 1-2). Light generated by the additional light source may be directed by the illumination subsystem to wafer 10 at a substantially normal angle of incidence. In this manner, the system embodiments described herein may be configured to have both oblique and normal illumination capability. The additional light source may include any of the light sources described herein, and the light generated by the additional light source may include any of the light described herein.

Light source 12 and the additional light source may be similarly or differently configured. The illumination subsystem may include a number of optical elements positioned in the path of the light from the additional light source. These optical elements may include any of those described above. Therefore, the illumination subsystem may be configured to direct light to the wafer at different angles of incidence simultaneously. In addition, although the illumination subsystem may be configured as described above to direct light to the wafer at an oblique angle of incidence and a substantially normal angle of incidence, the illumination subsystem may also or alternatively be configured to direct light to the spot on the wafer at two different oblique angles of incidence.

The illumination subsystem may also include a single light source that is used to provide light for illumination at multiple angles of incidence. For example, a single light source such as a multi-wavelength laser may be coupled to a beam splitter (not shown in FIGS. 1-2). The beam splitter may be configured to split the light from the laser into separate beams having different wavelengths, one of which is used for normal illumination and the other of which is used for oblique illumination. The illumination subsystem may include any other suitable combination of a single light source and beam multiplier(s) known in the art. In any of the above embodiments, the light used for oblique illumination may have one or more characteristics such as wavelength and/or polarization that are different than the characteristics of the light used for normal illumination. Alternatively, the light used for oblique illumination may have substantially the same characteristics as the light used for normal illumination.

In one embodiment, the system includes stage 18 shown in FIG. 1 configured to rotate (as shown by arrow 20) and translate the wafer while the light is directed to the spot on wafer 10 by the illumination subsystem such that the light directed to the spot is scanned across the wafer. In this manner, wafer 10 may be supported on stage 18, which may be rotated and translated such that the light illuminates a spot on the wafer that moves in a spiral path. For instance, stage 18 shown in FIG. 1 may provide motion in the x direction. The stage supports the wafer and may be mounted on top of a spindle (not shown in FIGS. 1-2). The spindle may provide rotation to the stage. In this manner, the system embodiments described herein may be configured for r/θ spiral scanning of the wafer. Alternatively, the light may be caused to move over the wafer in any manner to trace the spiral path or another type of scan path across the wafer. For example, the system may be configured to scan the light directed to the spot on the wafer across the wafer in the x and y directions.

Illumination of the wafer will cause scattering of the light from the wafer. In addition, if oblique incidence light and normal incidence light are used to illuminate the wafer, both oblique incidence light and normal incidence light will be scattered from the wafer.

The system includes a first detection subsystem configured to detect light scattered from one portion of the spot on the wafer and to generate output responsive to the detected light. In one embodiment, the first detection subsystem includes ellipsoidal collector 22 shown in FIG. 1 (a "panoramic" collector) configured to collect the light scattered from the one portion of the spot on the wafer. The first detection subsystem also includes detector 24, which in combination with ellipsoidal collector 22 form a "wide channel" of the system. In other words, light scattered from the one portion of the spot on the wafer along directions relatively far from normal to the surface of the wafer is collected and focused by ellipsoidal collector 22. For example, the relatively large panoramic ellipsoidal collector may be configured to collect scattered light at polar angles between about 25 degrees from normal to the surface of the wafer and about 75 degrees from normal to the surface of the wafer. In this manner, ellipsoidal collector 22 collects light scattered from the one portion of the spot at relatively "wide" scattering angles. Ellipsoidal collector 22 may be an ellipsoidal mirror configured to direct the collected light to detector 24. Detector 24 may include any suitable detector such as a photomultiplier tube (PMT). In addition, detector 24 may include a non-imaging detector (such as a PMT) such that the first detection subsystem is configured as a non-imaging detection subsystem. Detector 24 is configured to generate output responsive to the detected light. The output generated by the detector may include any suitable output such as analog signals responsive to the scattered light detected by the detector.

The first detection subsystem may also include a beam splitter (not shown in FIGS. 1-2) configured to direct one portion of the light collected by the ellipsoidal collector to detector 24 and the other portion of the collected light to another detector (not shown in FIGS. 1-2). One detector may be used to detect light scattered at relatively wide angles due to illumination by the normal incidence beam, and the other detector may be used to detect light scattered at relatively wide angles due to the illumination by the oblique incidence beam. The two detectors may include PMTs. The two detectors may also include non-imaging detectors. In addition, the two detectors may be similarly or differently configured. The first detection subsystem may include any other suitable optical elements (not shown in FIGS. 1-2). For example, one or more polarizers, one or more apertures, one or more spectral filters, and the like may be placed in the path of the collected light. In addition, the first detection subsystem may include any other suitable hardware or software (not shown in FIGS. 1-2) (e.g., an analog gain stage, an analog-to-digital converter (ADC), and digital processing).

The system also includes a second detection subsystem configured to separately and simultaneously detect light scattered from different portions of the spot on the wafer and to separately generate different output responsive to the separately detected light. In one embodiment, the second detection subsystem includes collector 26 configured to collect the light scattered from the different portions of the spot. In one such embodiment, the collector is not a high numerical aperture (NA) collector. More specifically, the collector may not have a high NA, which is generally considered greater than about 0.9 for inspection applications. For example, the collector may have an NA of about 0.3 to about 0.8. In one such example, the collector may have an NA of about 0.5. However, the collector may have any other suitable NA (e.g., an NA greater than about 0.8, etc.).

Collector 26 may include any suitable refractive optical element. In addition, collector 26 may be replaced with two or more refractive optical elements and/or one or more reflective optical elements, which may include any suitable refractive and/or reflective optical element(s) arranged in any suitable configuration. For example, such refractive optical element(s) may include, but are not limited to, a tube lens, a relay lens, a collimating lens, a focusing lens, a condenser lens, or some combination thereof.

The second detection subsystem may also include polarizer 28, aperture 30, refractive optical element 32, and beam splitter 34. Light collected by collector 26 is directed to polarizer 28, which may include any suitable polarizer. Light exiting polarizer 28 is directed to aperture 30, which may include any suitable aperture. In addition, aperture 30 may be an adjustable aperture or may be replaced with multiple adjustable apertures. For example, adjustable apertures may be used inside the collector of the second detection subsystem. The adjustable aperture(s) may be employed to further increase sensitivity to various defects of interest. Light exiting aperture 30 is directed to refractive optical element 32. Refractive optical element 32 may be configured as described above with respect to collector 26. Light from refractive optical element 32 may be directed to beam splitter 34, which may be configured to split the light from refractive optical element 32 into two different beams of light. Beam splitter 34 may include any suitable beam splitter.

In one embodiment, the second detection subsystem includes detector 36 configured to separately and simultaneously detect the light scattered from the different portions of the spot. For example, one beam of light exiting beam splitter 34 may be directed to detector 36 that is configured to separately and simultaneously detect the light scattered from the different portions of the spot. In one such embodiment, the detector includes a multi-anode PMT. In another such embodiment, the detector includes physically separated detection elements. For example, the anodes of a multi-anode PMT are physically separated from each other, and detection elements of other multi-detection element detectors described herein may be physically separated from each other. In one such example, as shown in FIG. 2, detector 36 may include detection elements 38 that are physically separated from one another.

The number of physically separated detection elements included in the detector preferably corresponds to the number of the different portions of the spot from which the scattered light is separately and simultaneously detected by the second detection subsystem such that each of the physically separated detection elements detects light scattered from only one of the different portions. In this manner, as described further herein, each of the anodes or detection elements included in the detector detects light scattered from only a relatively small portion of the illumination spot thereby achieving a "multi-spot" effect. In addition, light scattered from different portions of the spot can be imaged by the detection subsystem onto different detection elements of the detector. In this manner, the second detection subsystem is configured as an imaging detection subsystem.

The detector may also include any other detector that includes multiple physically separated detection elements. For example, the detector may include a charge coupled device (CCD) or a pin diode array (although the sensitivity of the system would be reduced by using such detectors). In addition, the multi-anode PMT may be replaced by an array of fibers configured to collect the light scattered from the different portions of the spot. In that case, the light at the other end of the fibers can be detected by, for example, multiple detectors such as discrete PMTs, a multi-anode PMT, discrete APD's, or a pin diode array. In this manner, the detector of the second detection subsystem may include an array detector and/or a fiber array.

In one embodiment, the second detection subsystem includes mask 35 positioned in front of detector 36 to increase optical separation between the physically separated detection elements. For example, the mask may be formed of a light blocking material having apertures (or holes) formed therethrough that limit the scattered light that reaches the detection elements thereby increasing the optical separation of the detection elements. In this manner, a mask may be placed in front of the multi-anode PMT (and each of the other multi-anode PMTs or detectors that include physically separated detection elements described herein that may be included in other detection subsystems described herein) to increase the optical separation between adjacent anodes. In another embodiment, the individual fiber elements may be packed next to each other, with no gaps between the adjacent elements. A lens array may be included in front of the fiber elements to concentrate the collected light into the correct fiber elements corresponding to a specific position along the illumination spot.

Detector 36 is configured to separately generate different output responsive to the separately detected light. For example, each of the anodes may separately generate different output responsive to the scattered light separately and simultaneously detected by each of the anodes. The different output generated by detector 36 may include any suitable output such as different analog signals responsive to the separately detected light.

As described above, the second detection subsystem may include collector 26 configured to collect the light scattered from the different portions of the spot. In one such embodiment, the second detection subsystem also includes a first detector configured to separately and simultaneously detect the collected light scattered from the different portions of the spot and a second detector configured to separately and simultaneously detect the collected light scattered from the different portions of the spot. For example, as shown in FIG. 1, the second detection subsystem may include detectors 36 and 40, each configured to separately and simultaneously detect the collected light scattered from the different portions of the spot. In particular, one portion of the collected light exiting beam splitter 34 may be directed to detector 36, and the other portion of the collected light exiting beam splitter 34 may be directed to detector 40. Detector 40 is configured to separately generate different output responsive to the separately and simultaneously detected light. The different output generated by detector 40 may include any suitable output such as different analog signals responsive to the separately detected light. Detector 40 may include any of the detectors described herein. For example, detector 40 may be a multi-anode PMT. In this manner, the second detection subsystem may include two multi-anode PMTs. Detector 40 may also be further configured as described herein.

In one embodiment, as shown in FIG. 1, the second detection subsystem is configured to detect the light scattered from the different portions at one or more polar angles that are closer to the wafer than polar angles at which the first detection subsystem detects the scattered light. For example, the second detection subsystem may be configured to detect the light scattered from the different portions at polar angles between about 75 degrees from the normal to the surface of the wafer and about 85 degrees from the normal to the surface of the wafer. In contrast, as described above, the first detection subsystem may be configured to detect the scattered light at polar angles between about 25 degrees from normal to the surface of the wafer and about 75 degrees from normal to the surface of the wafer. However, any and all of the detection subsystems and/or collectors described herein may be configured to subtend any polar angles desired.

The entire collection space of the second detection subsystem spans only a portion of the azimuthal angles at which the first detection subsystem detects the scattered light. For example, the ellipsoidal collector of the first detection subsystem may collect light across an azimuthal angle range of about 360 degrees. In contrast, the entire collection space of the second detection subsystem may span an azimuthal angle range of about 10 degrees to about 100 degrees.

In one embodiment, the one portion of the spot has an area on the wafer that is approximately equal to the entire area of the spot on the wafer. For example, the first detection subsystem may be configured to collect and detect light scattered from the entire area of the spot on the wafer. In this manner, the first detection subsystem "sees" the whole spot. Such a configuration of the first detection subsystem may be advantageous in that the maximum amount of scattered light can be detected by the first detection subsystem thereby maximizing the sensitivity of the system for detecting defects using the output generated by the first detection subsystem.

The spot may have any suitable dimensions on the wafer. In addition, if an existing inspection system is modified to include the second detection subsystem (and/or other detection subsystems described further herein), the dimensions of the illuminated spot on the wafer normally used by the inspection system may be modified. For example, the collection space of the first detection subsystem may be reduced (e.g., by reducing the collection space of the ellipsoidal collector) to accommodate the second detection subsystem (e.g., to accommodate the collector of the second detection subsystem). In one such example, a certain part of the ellipsoidal collector included in the SPx (e.g. SP1, SP2, etc.) systems commercially available from KLA-Tencor, San Jose, Calif., may be removed to accommodate the collector and any other optical elements of the second detection subsystem. As such, the collection space of the second detection subsystem may be "taken out of" the collection space of the ellipsoidal collector. Any reduction of sensitivity of the first detection subsystem due to a reduced collection space can be compensated for by a reduction in the optical spot size. For example, to enhance the sensitivity of the system on ultra smooth surfaces and also to compensate for the reduction in the collection space of the large, ellipsoidal collector, the width of the illumination spot may be reduced (e.g., by a factor of about two).

Figure 3:
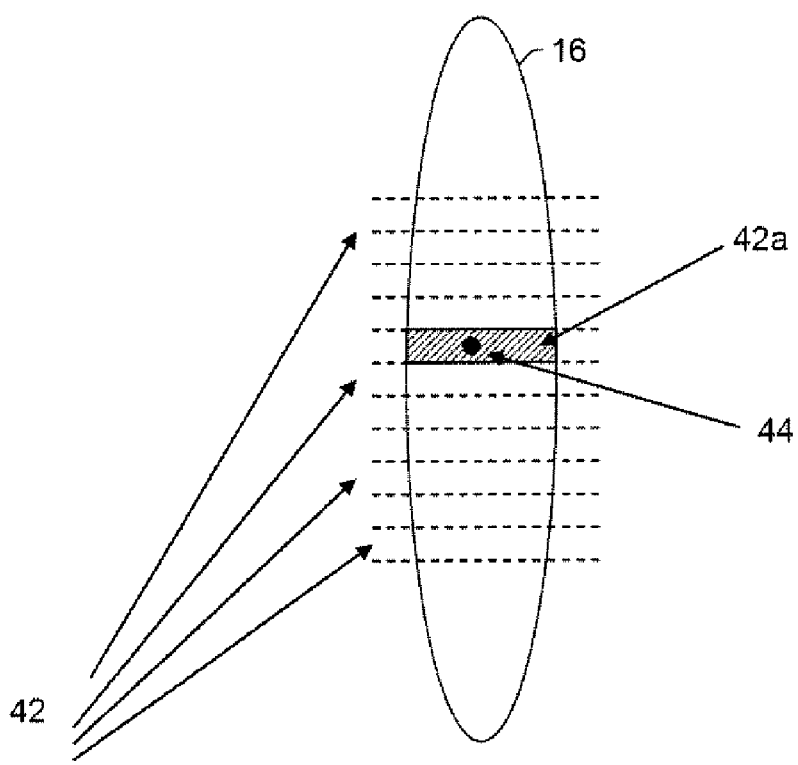
FIG. 3 is a schematic diagram illustrating a plan view of one embodiment of a spot on a wafer to which light is directed by an illumination subsystem embodiment described herein and different portions of the spot.

In one embodiment, an area of the one portion of the spot is larger than an area of each of the different portions of the spot. For example, as described above, the one portion of the spot may include substantially the entire spot. In addition, as described further herein, each of the different portions of the spot preferably includes an area of the spot that is less than the entire area of the spot. For example, as shown in FIG. 3, the illumination subsystem may be configured to direct light to spot 16 on a wafer (not shown in FIG. 3). Since the illumination subsystem is configured to direct the light to the spot at an oblique angle of incidence, the spot has an elliptical shape on the wafer. (However, the spot may have a different shape on the wafer (e.g., a line shape on the wafer)).

The area of the one portion of the spot from which scattered light is detected by the first detection subsystem may include approximately the entire area of the spot. In addition, different portions 42 may be defined within the spot on the wafer. In particular, at least a portion of the spot may be divided into the different portions. Different portions 42 extend along substantially an entire dimension of the spot in one direction but only a portion of an entire dimension of the spot in an opposite direction. For example, each of the different portions may extend across the entire dimension of the spot in the direction of the minor axis of the spot, and each of the different portions may extend across only a portion of the entire dimension of the spot in the direction of the major axis of the spot. In this manner, the different portions may be arranged in a one-dimensional array within the spot. In addition, as described above, each of the physically separated detection elements of the detector included in the second detection subsystem corresponds to only one of the different portions of the spot. In this manner, the detector of the second detection subsystem may include a one-dimensional array of physically separated detection elements, each of which corresponds to only one of the different portions in the one-dimensional array within the spot.

Although a particular number of different portions are shown in FIG. 3, the spot may be divided into any suitable number of different portions. As shown in FIG. 3, since the dimension of the spot in the direction of the minor axis varies along the major axis of the spot, some of the different portions may have different dimensions in the direction of the minor axis of the spot. In addition, as shown in FIG. 3, each of the different portions may have the same dimension in the direction of the major axis of the spot. However, at least some of the different portions may have different dimensions in the direction of the major axis of the spot (e.g., such that an area of each of the different portions on the wafer is substantially equal).

In one embodiment, none of the different portions within the spot overlap any other of the different portions within the spot. For example, as shown in FIG. 3, the different portions may be defined within the spot such that the different portions are adjacent to one another without any overlap between adjacent different portions. Although each of the different portions is shown in FIG. 3 as being adjacent to neighboring different portions, the different portions may be defined such that there is space between neighboring different portions. The space between the neighboring different portions may vary depending on the physical and/or optical separation between the detection elements of any detector included in the second detection subsystem (e.g., the space may be substantially equal to the physical and/or optical separation).

In some embodiments, the different portions in combination extend across an area within the spot that is smaller than the entire area of the spot. For example, as shown in FIG. 3, in the direction of the major axis of the spot, the different portions extend across only the central portion of the spot. In other words, the different portions do not extend across the entire dimension of the spot in the direction of the major axis of the spot. In this manner, the second detection subsystem may form an image of only the central part of the single illumination spot. Such a configuration of the different portions may be advantageous such that the intensity of the light that illuminates each of the different portions may be substantially the same. For example, the intensity of the light illuminating the spot on the wafer may be lower near the ends of the spot along the dimension of the spot in the direction of the major axis of the spot. The intensity gradient across the spot may vary depending on a number of variables such as the intensity distribution of the light from the light source, the configuration of the optical elements included in the illumination subsystem, the oblique angle of incidence at which the light is directed to the wafer, etc. Therefore, the area of the central portion of the spot across which the different portions in combination extend may be determined based on such variables such that the intensity of the light illuminating each of the different portions is substantially the same.

As described above, the area of each of the different portions of the spot may be less than the area of the spot itself. For example, as shown in FIG. 3, each different portion 42 has an area that is substantially less than the area of spot 16. In addition, as described further herein, light scattered from each of the different portions is separately and simultaneously detected and output responsive to such scattered light is separately generated. For example, different portions 42 of the illumination spot may be imaged onto different detector elements. As such, each of the detection elements of a detector (or detectors) of the second detection subsystem receives light from only a relatively small region of the illuminated field. Therefore, the second detection subsystem effectively collects and detects light from multiple spots (within a single spot) on the wafer simultaneously. In this manner, the second detection subsystem simulates the effect of multi-spot technology.

The multi-spot inspection of the wafer that can be performed by the second detection subsystem is advantageous for a number of reasons. For instance, each of the different portions of the spot has a smaller area on the wafer than the entire area of the spot on the wafer. Therefore, the ratio of the area of a defect on the wafer to the area of one of the different portions is greater than the ratio of the area of the same defect to the area of the entire spot. In other words, a greater area within a different portion will be occupied by a defect than the area within the entire spot that would be occupied by the same defect. For instance, as shown in FIG. 3, a greater portion of the area of different portion 42a is occupied by defect 44 than the portion of the area within the entire spot 16 that is occupied by the same defect.

In this manner, portion 42a giving background scattering to the detection element that detects the scattering from defect 44 is much less than the background scattering that would be produced by the entire spot. More specifically, within each of the different portions, the area of the surface of the wafer that is illuminated is less than the area of the surface of the wafer that is illuminated by the entire spot. As such, within each of the different portions, less light will be scattered by the wafer surface than that which would be scattered by the wafer surface within the entire spot. In this manner, the scattering due to the defect increases as the optical spot size is reduced since the light intensity increases (i.e., a greater portion of the intensity intersects the defects, which are typically much smaller than the spot size). Therefore, the light scattered from each of the different portions that is collected and separately detected by the second detection subsystem will include less light scattered from the wafer surface relative to the light scattered from any defect located within each of the different portions.

In this manner, although the light scattered by a defect is collected into each collector and, depending on its location, is delivered to a specific detection element of the detector, only that portion of the background scattering that corresponds to the size of the different portion on the wafer gives rise to background "noise." Consequently, the defect signal-to-noise ratio of output responsive to the light scattered from a different portion in which a defect is located will be greater than the defect signal-to-noise ratio of output responsive to the light scattered from the entire spot. The signal-to-noise ratio (S/N), therefore, improves. As such, defects on the wafer can be detected with greater sensitivity using the output generated by the second detection subsystem. In this manner, the system embodiments described herein are configured as enhanced sensitivity inspection systems. In addition, the embodiments described herein achieve a sensitivity enhancement in detecting relatively small defects on both smooth and rough surfaces.

The embodiments described herein have a number of additional advantages. For example, as described further herein, the second detection subsystem simulates the effect of multi-spot technology using only a single obliquely illuminated spot (or line) on a wafer. Therefore, using this approach, the system provides advantages such as enhanced sensitivity for defect detection as described above while maintaining inspection system throughput.

In one embodiment, the second detection subsystem is configured to preserve information about the different portion of the spot from which the separately detected light was scattered and to not preserve information about polar and azimuthal angles within the entire collection space of the second detection subsystem at which the light was scattered from the different portions of the spot. For example, the light scattered from one of the different portions may be directed to only one of the physically separated detection elements of the detector of the second detection subsystem. As such, the second detection subsystem may preserve information about the different portion of the spot from which the separately detected light was scattered. More specifically, since each of the physically separated detection elements corresponds to only one of the different portions of the spot, the output generated by each of the physically separated detection elements corresponds to only one of the different portions. As such, the output separately generated by different elements of the detector contains information about the different portions from which the light was scattered. However, all of the light scattered from one of the different portions that is collected by the second detection subsystem is directed to the same detection element of the detector. As such, information about the polar and azimuthal angles within the entire collection space of the second detection subsystem at which the light was scattered from the different portions of the spot is not preserved by the second detection subsystem.

In one embodiment, the second detection subsystem is configured such that the different output separately generated by the second detection subsystem is substantially unaffected by movement of the wafer in a direction substantially perpendicular to a surface of the wafer being inspected. For example, if there is a z-movement of the wafer, the beam of light directed to the wafer at an oblique angle of incidence by the illumination subsystem will move on the surface of the wafer. In particular, when the wafer moves up or down, the intersection of the optical axis of the oblique illumination beam and the wafer surface will move in a line in the plane of incidence of the oblique illumination beam. However the imaging collector of the second detection subsystem is "looking at" the illuminated area from the side as described further herein. As such, if there is a defect on the surface, and there is movement of the wafer up or down, the position of the defect with respect to the side imaging system only moves up or down, not sideways. All that happens is that a different part of the beam illuminates the defect. As such, the image of a scatterer (e.g., a defect) will only move up and down on the detector of the second detection subsystem (e.g., up and down on the anodes) and will, therefore, not have an adverse effect on the detection.

In one embodiment, the second detection subsystem includes a first detector (e.g., detector 36 shown in FIG. 1) configured to separately and simultaneously detect the light scattered from the different portions of the spot and a second detector (detector 40) configured to separately and simultaneously detect the light scattered from the different portions of the spot. The first and second detectors may be further configured as described above. In one such embodiment, the first and second detectors are positioned such that there is a half pixel shift between the first and second detectors.

Figure 4:
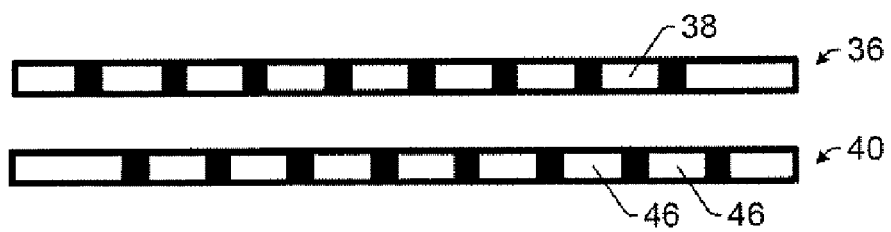
FIGS. 4-5 are schematic diagrams illustrating a plan view of different embodiments of first and second detectors that may be included in an embodiment of a detection subsystem described herein.

One such embodiment of the first and second detectors is shown in FIG. 4. For example, as shown in FIG. 4, detector 36 may include detection elements 38 that are physically separated from each other. Detector 40 also includes detection elements 46 that are physically separated from each other. In this manner, detectors 36 and 40 may be detector arrays. FIG. 4 shows the lateral positioning of the channels in the detector arrays with respect to the detection space of the second detection subsystem. For example, as shown in FIG. 4, the detectors are positioned such that there is a half pixel shift between the first and second detectors. In other words, one detection element of one of the detectors overlaps at least one detection element of the other detector in detection space. In this manner, the two detectors (e.g., two multi-anode PMTs) may be positioned on either side of the center of the illumination spot such that there is a half pixel shift between the two detectors. Such a configuration ensures that the "dead" spaces between adjacent detection elements (e.g., anodes) do not render the system blind to defects whose positions happen to correspond to these dead spaces. As such, the lateral positioning of the specific detector arrays or arrays of detection elements with respect to each other can ensure that there are no "blind" spots (e.g., areas within the illumination spot) in which scattered light falls between any two adjacent detection elements.

Figure 5:
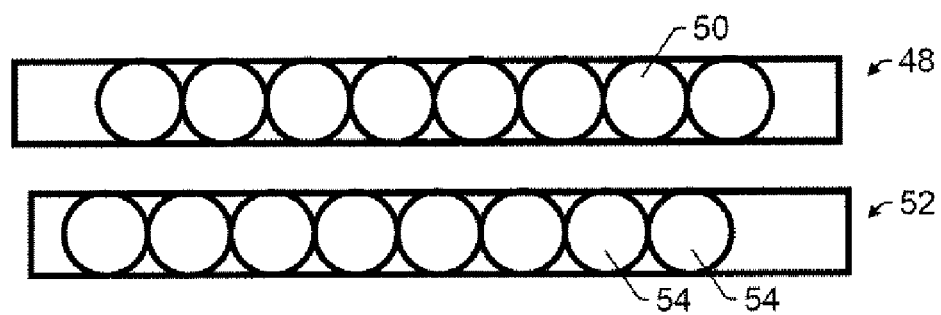

Another such embodiment of the first and second detectors is shown in FIG. 5. For example, as shown in FIG. 5, detector 48 may include an array of optical fibers 50, which may be configured as described above. For example, each of the optical fibers may be configured to direct light scattered from only one of the different portions to a different detection element of a single detector or a different detector. In this manner, the detector may include an array of fibers going to individual detection channels. The optical fibers may be physically separated from each other by the cladding surrounding the core of each of the optical fibers. Detector 52 also includes an array of optical fibers 54, which may be configured as described above. FIG. 5 shows the lateral positioning of the channels in the detector arrays with respect to the detection space of the second detection subsystem. For example, as shown in FIG. 5, the different arrays of optical fibers are positioned such that there is a half pixel shift between the different arrays. In this manner, one optical fiber of one of the arrays overlaps at least one optical fiber of the other array in detection space. As such, one detection element or detector of one of the detectors will also overlap at least one detection element or detector of the other detector in detection space. In this manner, the two fiber arrays may be positioned on either side of the center of the illumination spot such that there is a half pixel shift between the two fiber arrays thereby producing a corresponding half pixel shift between the detectors configured to detect the light collected by the two fiber arrays. Such a configuration ensures that the "dead" spaces between adjacent fibers do not render the system blind to defects whose positions happen to correspond to these dead spaces. As such, the lateral positioning of the specific is fiber arrays with respect to each other can ensure that there are no "blind" spots (e.g., areas within the illumination spot) in which scattered light falls between any two adjacent fibers and therefore falls between any two adjacent detection elements or any two adjacent detectors.

Figure 6:
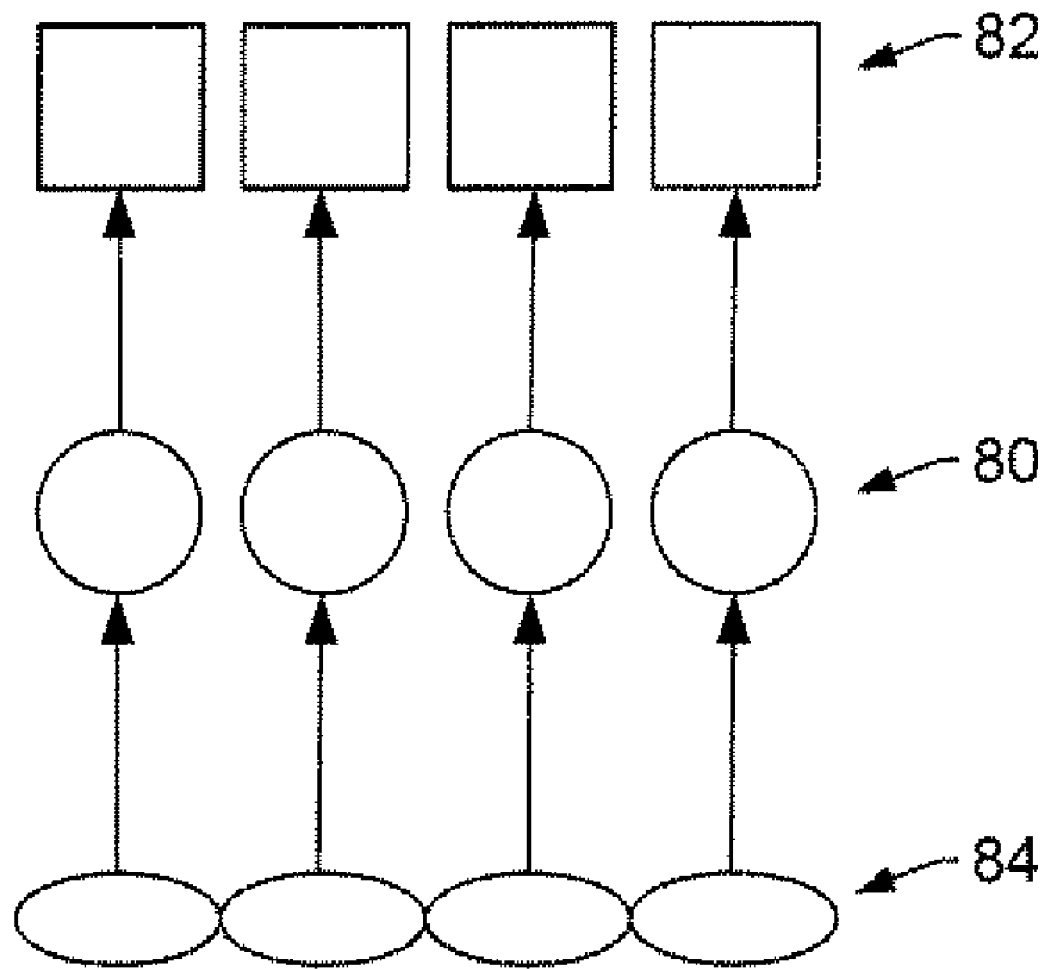
FIG. 6 is a block diagram illustrating one embodiment of optical fibers, detection elements, and micro-lenses that may be included in a second detection subsystem of the system embodiments described herein.

In another embodiment, the second detection subsystem includes optical fibers configured to separately and simultaneously direct the light scattered from the different portions to different detection elements such that the different detection elements separately and simultaneously detect the light scattered from the different portions of the spot. For example, as shown in FIG. 6, the second detection subsystem may include optical fibers 80 configured to separately and simultaneously direct the light scattered from the different portions to different detection elements 82 such that the different detection elements separately and simultaneously detect the light scattered from the different portions. The different detection elements may include different detection elements of a single detector or different detection elements of different detectors. The optical fibers may include any suitable optical fibers arranged in any suitable array. Any suitable numbers of optical fibers and detection elements may be included in the second detection subsystem. In addition, the number of optical fibers included in the second detection subsystem may be equal to the number of different detection elements included in the second detection subsystem. The optical fibers and the detection elements may be further configured as described herein.

In one such embodiment, the second detection subsystem includes micro-lenses positioned in front of the optical fibers and configured to eliminate dead spaces between adjacent optical fibers. For example, as shown in FIG. 6, the second detection subsystem may include micro-lenses 84 positioned in front of optical fibers 80 (in the path of the scattered light collected by the optical fibers) and configured to eliminate dead spaces between adjacent optical fibers. The micro-lenses may include any suitable micro-lenses arranged in any suitable array. Any suitable number of micro-lenses may be included in the second detection subsystem. In addition, the number of micro-lenses included in the second detection subsystem may be equal to the numbers of optical fibers and different detection elements included in the second detection subsystem. In this manner, the second detection subsystem may use a micro-lens array, placed in front of a fiber array to completely eliminate the "dead" space between adjacent fibers. As such, the micro-lenses can ensure that there are no "blind" spots (e.g., areas within the illumination spot) in which the scattered light falls between any two adjacent fibers and therefore falls between any two adjacent detection elements or any two adjacent detectors.

In one embodiment, the illumination subsystem is configured to direct the light to the spot on the wafer at the oblique angle of incidence and a first azimuthal angle, and the second detection subsystem is configured to separately and simultaneously detect the light scattered from the different portions of the spot at one or more azimuthal angles different than the first azimuthal angle. In one such embodiment, the first azimuthal angle and the one or more azimuthal angles are not opposite to each other. In this manner, the second detection subsystem may be configured as a side detection channel (or a "side collector" or "side channel").

The second detection subsystem may also be arranged in a "double dark field" configuration. For example, as shown in FIG. 2, the illumination subsystem is configured to direct the light to the spot on the wafer at the oblique angle of incidence and a first azimuthal angle. In addition, the second detection subsystem is configured to separately and simultaneously detect the light scattered from the different portions of the spot at one or more azimuthal angles defined by azimuthal angles across which collector 26 collects light. Therefore, as shown in FIG. 2, the azimuthal angle at which the illumination subsystem directs light to the spot on the wafer is different than the azimuthal angles across which collector 26 collects light and therefore is different than the azimuthal angles across which the second detection subsystem detects light. In addition, as shown in FIG. 2, the azimuthal angle at which the illumination subsystem directs light to the spot on the wafer is not opposite to any of the azimuthal angles across which collector 26 collects light and is therefore not opposite to any of the azimuthal angles across which the second detection subsystem detects light. For example, as shown in FIG. 2, the azimuthal angle at which the illumination subsystem directs light to the spot on the wafer is separated by about 90 degrees from the azimuthal angle at which the center of collector 26 is positioned.

In one embodiment, the light directed to the spot on the wafer at the oblique angle of incidence by the illumination subsystem includes s-polarized light, and the light scattered from the different portions of the spot separately and simultaneously detected by the second detection subsystem includes s-polarized light. For example, light source 12 may be configured to generate s-polarized light such that the light directed to the spot on the wafer by the illumination subsystem at the oblique angle of incidence includes s-polarized light. Alternatively, the illumination subsystem may include a polarizer (not shown) that is configured to alter the polarization of the light generated by the light source such that the light directed to the spot on the wafer by the illumination subsystem at the oblique angle of incidence includes s-polarized light. Such a polarizer may include any suitable polarizer and may vary depending on the polarization of the light generated by the light source. In addition, polarizer 28 included in the second detection subsystem may be configured such that the light scattered from the different portions of the spot separately and simultaneously detected by the second detection subsystem includes s-polarized light. Polarizer 28 may include any suitable polarizer that can be configured in this manner. In this manner, the second detection subsystem may be configured to detect defects using an S-S polarization combination, which may be particularly advantageous for the double dark field arrangement described above. As such, the side collector allows S-S double dark field inspection to be performed, which is a geometry that is particularly suitable for inspecting rough surfaces.

However, the polarization of the illumination and the polarization of the detection may include all other types of polarization combinations. For example, the light directed to the wafer by the illumination subsystem may be s-polarized light (e.g., only s-polarized light), p-polarized light (e.g., only p-polarized light), or circularly polarized light (e.g., a linear combination of p-polarized light and phase-shifted s-polarized light). In addition, the light scattered from the different portions of the spot on the wafer that is separately and simultaneously detected by the second detection subsystem may include s-polarized light (e.g., only s-polarized light), p-polarized light (e.g., only p-polarized light), or circularly polarized light (e.g., a linear combination of p-polarized light and phase-shifted s-polarized light).

In one such example, the light directed to the spot on the wafer at the oblique angle of incidence by the illumination subsystem may include p-polarized light, and the light scattered from the different portions of the spot separately and simultaneously detected by the second detection subsystem may include p-polarized light. In another such example, the light directed to the spot on the wafer at the oblique angle of incidence by the illumination subsystem may include s-polarized light, and the light scattered from the different portions of the spot separately and simultaneously detected by the second detection subsystem may include unpolarized light (e.g., light detected by the second detection subsystem when a polarizer and/or analyzer is not positioned in path(s) of the light scattered from the wafer that is detected by the second detection subsystem). In a further such example, the light directed to the spot on the wafer at the oblique angle of incidence by the illumination subsystem may include p-polarized light, and the light scattered from the different portions of the spot separately and simultaneously detected by the second detection subsystem may include unpolarized light (e.g., light detected by the second detection subsystem when a polarizer and/or analyzer is not positioned in path(s) of the light scattered from the wafer that is detected by the second detection subsystem).

The second detection subsystem may include any other suitable optical elements (not shown in FIGS. 1-2). For example, one or more spectral filters may be placed in the path of the scattered light collected by the second detection subsystem. In addition, the second detection subsystem may include any other suitable hardware and software (not shown in FIGS. 1-2) (e.g., one or more analog gain stages, one or more ADCs, and digital processing hardware and/or software).

The system also includes a computer subsystem configured to detect defects on the wafer using the output generated by the first detection subsystem and the different output separately generated by the second detection subsystem. For example, as shown in FIG. 1, the system includes computer subsystem 56. The output generated by the first detection subsystem may be provided to the computer subsystem. For example, computer subsystem 56 may be coupled to detector 24 of the first detection subsystem (e.g., via one or more transmission media, which may include any suitable transmission media known in the art, as shown by the dotted line in FIG. 1). The computer subsystem may be coupled to the detector such that the computer subsystem can receive the output generated by the detector. In addition, if the first detection subsystem includes additional elements such as an analog gain stage, an ADC, and digital processing, the computer subsystem may be coupled to one of the additional elements such that the computer subsystem can receive the output generated by the detector. If the first detection subsystem includes more than one detector, the computer subsystem may be coupled to each of the detectors as described above. The computer subsystem may be configured to use the output generated by the first detection subsystem and any suitable algorithm and/or method to detect the defects on the wafer.

In a similar manner, the different output separately generated by the second detection subsystem may be provided to the computer subsystem. For example, computer subsystem 56 may be coupled to detectors 36 and 40 of the second detection subsystem (e.g., via one or more transmission media, which may include any suitable transmission media known in the art, as shown by the dotted lines in FIG. 1). The computer subsystem may be coupled to the detectors such that the computer subsystem can receive the different output separately generated by the detectors. In addition, if the second detection subsystem includes additional elements such as analog gain stage(s), ADC(s), and digital processing hardware and/or software, the computer subsystem may be coupled to one or more of the additional elements such that the computer subsystem can receive the output generated by the detectors. The computer subsystem may be configured to use the different output separately generated by the detectors and any suitable algorithm and/or method to detect the defects on the wafer. In addition, the computer subsystem may be configured to separately process the different output separately generated by the second detection subsystem using any suitable method and/or algorithm to detect the defects on the wafer. Furthermore, computer subsystem 56 may be configured to separately process the output generated by the first detection subsystem and the different output separately generated by the second detection subsystem using any suitable method and/or algorithm to detect the defects on the wafer.

The computer subsystem may also be configured to perform any other inspection-type functions using the output generated by the first detection subsystem and/or the different output separately generated by the second detection subsystem. For example, as described above, the second detection subsystem may be configured as an imaging detection subsystem. Therefore, the different output separately generated by the second detection subsystem corresponding to a defect on the wafer may contain information regarding the type of the defect. In this manner, the computer subsystem may be configured to use the different output separately generated by the second detection subsystem (possibly in combination with the output generated by the first detection subsystem and/or other detection subsystems described herein) to classify defects detected on the wafer.

In one embodiment, the computer subsystem is configured to perform a convolution of the different output separately generated by the second detection subsystem and to detect the defects on the wafer using results of the convolution. For example, a 2×1 convolution can be performed on the different separately generated output to generate a more uniform detection signal for a given defect regardless of the specific location of the defect with respect to the detection elements of a detector or detectors. More specifically, the collected light that falls onto the detector(s) of the second detection subsystem will give rise to a signal in each of the detection elements of the detector(s). If the collected light scattered from a defect happens to fall onto one detection element (e.g., one pixel) of a detector, that specific detection element generates a signal due to all of the light. If, on the other hand, the defect happens to be in a location such that the collected light scattered from the defect falls in between two adjacent detection elements of the detector, then clearly the defect produces two signals, one from each detection element. Therefore, the same size defect can produce substantially different signal levels depending on the position of the defect within the field of view of the system. To alleviate such issues, the computer subsystem may perform a 2×1 convolution across the detection elements. Basically, the convolution amounts to having a "moving window" two detection elements wide across the detector. In that case, the registered output from any detection element is essentially the average of the output of the two adjacent detection elements thereby resulting in more or less constant defect signal levels regardless of where the light scattered from the defect falls on the detection elements. The computer subsystem may be configured to perform the convolution using any suitable method and/or algorithm.

The convolution may be performed prior to defect detection. For example, the computer subsystem may perform the convolution and then set the threshold of a defect detection algorithm to see which events pass the threshold. As described above, if the computer subsystem performs a convolution, then the signal levels are much more uniform for the same defect size regardless of where the defect is located. On the other hand, if the computer subsystem does not perform the convolution, then in most instances, the signal level of the defect will be higher, but there will be occasions in which the signal is split between two adjacent detection elements, which could reduce the capture rate of the defects.

If the computer subsystem is configured to perform the convolution as described above, each of the detection subsystems included in the system that is configured to separately and simultaneously detect light scattered from the different portions of the spot may include only one detector instead of two as described in some embodiments herein. For example, including two sets of detectors in each of the detection subsystems configured to simulate multi-spot inspection ensures that one is always able to get the maximum signal for a defect regardless of where the defect is positioned within the field of view of the system. However, since the light collected by each of such detection subsystems is split by a beam splitter to direct the light to the two detectors, the collected light is split into two parts thereby reducing the inherent sensitivity of the system. Instead, each detection subsystem may include only one detector, and the computer subsystem may be configured to perform a convolution on the different output separately generated by the detector.

The computer subsystem may take various forms, including a personal computer system, image computer, mainframe computer system, workstation, network appliance, Internet appliance, or other device. In general, the term "computer subsystem" may be broadly defined to encompass any device having one or more processors, which executes instructions from a memory medium. The computer subsystem may also include any suitable processor known in the art such as a parallel processor. In addition, the computer subsystem may include a computer platform with high speed processing and software, either as a standalone or a networked tool.

In some embodiments, the computer subsystem may be configured to store all of the output generated by one or more of the detection subsystems for the entire wafer or the entire portion of the wafer that is scanned during inspection and to determine one or more characteristics of the wafer using all of the stored output for the wafer. In some such embodiments, the computer subsystem may be configured to determine variations in a characteristic over the entire wafer or the entire portion of the wafer that is scanned as a function of position across the wafer. In additional such embodiments, the computer subsystem may be configured to determine the one or more characteristics using all of the stored output for the wafer (e.g., an average value or some statistical value of a characteristic across the entire wafer or the entire portion of the wafer). In such embodiments, the computer subsystem may be configured as described in commonly owned U.S. Patent Application Ser. No. 60/974,030 by Bhaskar et al. filed Sep. 20, 2007, which is incorporated by reference as if fully set forth herein. The embodiments described herein may be configured to perform any step(s) of any method(s) described in this patent application.

In one embodiment, the system includes a third detection subsystem configured to separately and simultaneously detect light scattered from the different portions of the spot on the wafer and to separately generate different output responsive to the scattered light separately detected by the third detection subsystem. Therefore, the third detection subsystem may have a configuration that is similar to that of the second detection subsystem except that the second and third detection subsystems detect light in different portions of the scattering hemisphere above the wafer. For example, in one embodiment, the second and third detection subsystems collect and detect the scattered light at different azimuthal angles. In addition, the different portions from which scattered light is separately and simultaneously detected by the third detection subsystem may include the same different portions from which the scattered light is separately and simultaneously detected by the second detection subsystem.

One embodiment of such a third detection subsystem is shown in FIGS. 1-2. For example, the third detection subsystem includes collector 58 configured to collect the light scattered from the different portions of the spot on wafer 10. Collector 58 may be further configured as described above. For example, in one embodiment, the collector is not a high NA collector. However, the collector may have any suitable NA. The third detection subsystem may also include polarizer 60, aperture 62, refractive optical element 64, and beam splitter 66. Light collected by collector 58 is directed to polarizer 60, which may include any suitable polarizer. Light exiting polarizer 60 is directed to aperture 62, which may include any suitable aperture. In addition, aperture 62 may be an adjustable aperture or may be replaced with multiple adjustable apertures. For example, adjustable apertures may be used inside the collector of the third detection subsystem. The adjustable aperture(s) may be employed to further increase sensitivity to various defects of interest. Light exiting aperture 62 is directed to refractive optical element 64. Refractive optical element 64 may be configured as described above with respect to collector 26. Light from refractive optical element 64 may be directed to beam splitter 66, which may be configured to split the light from refractive optical element 64 into two different beams of light. Beam splitter 66 may include any suitable beam splitter.

In one embodiment, the third detection subsystem includes detector 68 configured to separately and simultaneously detect the light scattered from the different portions of the spot. For example, one beam of light exiting beam splitter 66 may be directed to detector 68 that separately and simultaneously detects the light scattered from the different portions of the spot. In one such embodiment, the detector includes a multi-anode PMT. In another such embodiment, the detector includes physically separated detection elements. The detector may also include any other multi-element detector described herein. For example, as shown in FIG. 2, detector 68 may include detection elements 70 that are physically separated from one another. In one such embodiment, the third detection subsystem includes a mask (not shown) positioned in front of detector 68 to increase optical separation between the physically separated detection elements. Detector 68 is configured to separately generate different output responsive to the separately detected light. The different output generated by detector 68 may include any suitable output such as different analog signals responsive to the separately detected light.

As described above, the third detection subsystem may include collector 58 configured to collect the light scattered from the different portions of the spot. In one such embodiment, the third detection subsystem also includes a first detector configured to separately and simultaneously detect the collected light scattered from the different portions of the spot and a second detector configured to separately and simultaneously detect the collected light scattered from the different portions of the spot. For example, as shown in FIG. 1 the third detection subsystem may include detectors 68 and 72, each configured to separately and simultaneously detect the collected light scattered from the different portions of the spot. In particular, one portion of the collected light exiting beam splitter 66 may be directed to detector 68, and the other portion of the collected light exiting beam splitter 66 may be directed to detector 72. Detector 72 is configured to separately generate different output responsive to the separately detected light. The different output separately generated by detector 72 may include any suitable output such as different analog signals responsive to the separately detected light. The first and second detectors may be further configured as described herein. For example, in one embodiment, the first and second detectors included in the third detection subsystem are positioned such that there is a half pixel shift between the first and second detectors. In addition, the first and second detectors included in the third detection subsystem may include any of the detectors described herein. For example, the third detection subsystem may include two multi-anode PMTs.

In one embodiment, as shown in FIG. 1, the third detection subsystem is configured to detect the light scattered from the different portions at one or more polar angles that are closer to the wafer than polar angles at which the first detection subsystem detects the scattered light. For example, the third detection subsystem may be configured to detect the light scattered from the different portions at polar angles between about 75 degrees from normal to the surface of the wafer and about 85 degrees from normal to the surface of the wafer. In contrast, as described above, the first detection subsystem may be configured to detect the scattered light at polar angles between about 25 degrees from normal to the surface of the wafer and about 75 degrees from normal to the surface of the wafer. However, any and all of the detection subsystems and/or collectors described herein may be configured to subtend any polar angles desired.

The entire collection space of the third detection subsystem spans only a portion of the azimuthal angles at which the first detection subsystem detects the scattered light. For example, the ellipsoidal collector of the first detection subsystem may collect light across an azimuthal angle range of about 360 degrees. In contrast, the entire collection space of the third detection subsystem may span an azimuthal angle range of about 10 degrees to about 100 degrees. As shown in FIGS. 1-2, the second and third detection subsystems collect and detect the scattered light at different azimuthal angles, and the second and third detection subsystems may be configured to collect and detect the scattered light at substantially opposite azimuthal angles.

The third detection subsystem may be further configured as described herein with respect to the second detection subsystem. For example, in one embodiment, the third detection subsystem is configured to preserve information about the different portion of the spot from which the separately detected light was scattered and to not preserve information about polar and azimuthal angles within the entire collection space of the third detection subsystem at which the light was scattered from the different portions of the spot. The third detection subsystem may be configured in this manner as described further herein. In another embodiment, the third detection subsystem is configured such that the different output separately generated by the third detection subsystem is substantially unaffected by movement of the wafer in a direction substantially perpendicular to a surface of the wafer being inspected. The third detection subsystem may be configured in such a manner as described further herein.

As described above, the illumination subsystem may be configured to direct the light to the spot on the wafer at the oblique angle of incidence and the first azimuthal angle. In one such embodiment, the third detection subsystem is configured to separately and simultaneously detect the light scattered from the different portions of the spot at one or more azimuthal angles different than the first azimuthal angle, and the first azimuthal angle and the one or more azimuthal angles are not opposite to each other. The third detection subsystem may be configured in this manner as described further herein.

In this manner, the third detection subsystem may be configured as a side detection channel (or a "side collector" or "side channel"). As such, the system may include two side collectors or channels (i.e., the second and third detection subsystems described above). As described above, a portion of the ellipsoidal collector may be removed to accommodate the collector and possibly other optical elements of the second detection subsystem. In a similar manner, another portion of the ellipsoidal collector may be removed to accommodate the collector and possibly other optical elements of the third detection subsystem. For example, cuts into the sides of the ellipsoidal collector may be made, and two imaging systems, which attempt to image the light scattered due to the different portions of the illumination region on the wafer into a number of detection elements or detectors, may be placed into the cuts. Preferably, the portions of the ellipsoidal collector that are removed to accommodate the two side collectors are as small as possible to minimize the reduction in the collection space of the ellipsoidal collector.

In another embodiment described further herein, the light directed to the spot on the wafer at the oblique angle of incidence by the illumination subsystem includes s-polarized light. In one such embodiment, the light scattered from the different portions of the spot separately and simultaneously detected by the third detection subsystem includes s-polarized light. The third detection subsystem may be configured in this manner as described further herein. However, the polarization of the illumination and the polarization of the detection may include all other types of polarization combinations including any of those described herein.

Embodiments of the system that include a third detection subsystem described above may also be further configured as described herein. For example, the computer subsystem may be coupled to the detector(s) of the third detection subsystem as shown by the dotted lines in FIG. 1. In addition, the computer subsystem may be configured to detect the defects on the wafer using the output generated by the first detection subsystem and the different output separately generated by the second and third detection subsystems as described further herein. Furthermore, the computer subsystem may be configured to perform a convolution on the different output separately generated by the third detection subsystem and to detect the defects on the wafer using results of this convolution.

In one embodiment, the system includes a third detection subsystem configured to detect light scattered from the one portion of the spot on the wafer and to generate output responsive to the scattered light detected by the third detection subsystem. This third detection subsystem is different than the third detection subsystem described above, and either or both of the "third" detection subsystems may be included in the system. This third detection subsystem includes a refractive collector positioned such that an optical axis of the refractive collector is substantially perpendicular to a surface of the wafer being inspected. For example, as shown in FIG. 1, this third detection subsystem includes lens collector 74 positioned such that an optical axis of the refractive collector is substantially perpendicular to the surface of the wafer being inspected by the system.

This third detection subsystem also includes mirror 76 and detector 78, which in combination with lens collector 74 form a "narrow" channel of the system. Therefore, this detection subsystem is referred to herein as the "narrow" channel of the system. In other words, light scattered from the one portion of the spot on the wafer along directions relatively close to normal to the surface of the wafer is collected and focused by lens collector 74. For example, the lens collector may be configured to gather the light scattered from the one portion of the spot on the wafer by collecting the scattered light at polar angles up to about 20 degrees from normal to the surface of the wafer. In this manner, lens collector 74 collects light scattered from the one portion of the spot on the wafer at relatively "narrow" scattering angles.

Lens collector 74 directs the collected light to mirror 76, which directs the light to detector 78. Detector 78 may include any suitable detector such as a PMT. In this manner, the detector included in this third detection subsystem may be a non-imaging detector. As such, this third detection subsystem may be configured as a non-imaging detection subsystem. Detector 78 is configured to generate output responsive to the detected light. The output generated by the detector may include any suitable output such as analog signals responsive to the scattered light detected by the detector.

The one portion of the spot from which this third detection subsystem collects and detects scattered light may be configured as described above. For example, the one portion of the spot may have an area on the wafer that is approximately equal to the entire area of the spot on the wafer. Therefore, like the first detection subsystem described above, this third detection subsystem may be configured to "see" the entire illuminated spot (or line) on the wafer.

This third detection subsystem may also include a beam splitter (not shown) configured to direct one portion of the light reflected by mirror 76 to detector 78 and another portion of the light to another detector (not shown). One detector may be used to detect light scattered at relatively narrow angles due to illumination by the normal incidence beam, and the other detector may be used to detect light scattered at relatively narrow angles due to illumination by the oblique incidence beam. The two detectors may include PMTs. In this manner, the detectors included in this third detection subsystem may be non-imaging detectors. As such, this third detection subsystem may be configured as a non-imaging detection subsystem. The two detectors may be similarly or differently configured. This third detection subsystem may include any other suitable optical elements (not shown). For example, one or more polarizers, one or more apertures, one or more spectral filters, and the like may be placed in the path of the collected light. In addition, a spatial filter may be included in the third detection subsystem to prevent the specular reflection of the normal incidence beam from reaching detector 78 and any other detector included in this third detection subsystem. Furthermore, this third detection subsystem may include any other suitable hardware or software (not shown) (e.g., an analog gain stage, an ADC, and digital processing).

The computer subsystem described above may be coupled to the detector(s) of the narrow channel as shown by the dotted line in FIG. 1 and as described further herein. The computer subsystem may be configured to detect defects on the wafer using the output generated by the narrow channel as described further herein. In addition, the computer subsystem may be configured to detect defects on the wafer and/or perform any other inspection-type function using some combination of the output generated by the first detection subsystem, one or both of the side detection subsystems, and the narrow channel as described further herein.

The general approach for simulating the effect of multi-spot technology described above (e.g., cutting out a certain part of the large ellipsoidal collector and segmenting the illumination spot or line in the detection space) is equally applicable in the so-called dark-narrow region of the collection system described above. For example, in some embodiments, the system includes a third detection subsystem configured to separately and simultaneously detect light scattered from the different portions of the spot on the wafer and to separately generate different output responsive to the scattered light separately detected by the third detection subsystem. In one such embodiment, the third detection subsystem includes a refractive collector positioned such that an optical axis of the refractive collector is substantially perpendicular to a surface of the wafer being inspected. In this manner, this third detection subsystem is different than the third detection subsystems described above in that this third detection subsystem does not include a side collector and simulates multi-spot technology, and any or all of the "third" detection subsystems described herein may be included in the system. For example, this third detection subsystem may include lens collector 74 shown in FIG. 1 positioned such that an optical axis of the refractive collector is substantially perpendicular to a surface of wafer 10 being inspected. In this manner, the narrow channel shown in FIG. 1 may be configured to separately and simultaneously detect light scattered from the different portions of the spot on the wafer and to separately generate different output responsive to the scattered light separately detected by the third detection subsystem. As such, the relatively small collector, which is positioned perpendicularly above the illumination spot, can also be used to image the illumination spot into smaller portions thereby enhancing the sensitivity in this region as well.

The narrow channel may be configured in this manner according to any of the embodiments described herein. For example, the narrow channel may be configured to preserve information about the different portion of the spot from which the separately detected light was scattered and to not preserve information about polar and azimuthal angles within the entire collection space of the narrow channel at which the light was scattered from the different portions of the spot. In addition, lens collector 74 included in the narrow channel may be configured to collect the light scattered from the different portions of the spot, and lens collector 74 may not be a high NA collector. However, the lens collector may have any suitable NA. The narrow channel may also include detector 78 configured to separately and simultaneously detect the light scattered from the different portions of the spot, and the detector may include a multi-anode PMT. In some embodiments, the narrow channel includes detector 78 configured to separately and simultaneously detect the light scattered from the different portions of the spot, and the detector includes physically separated detection elements. In one such embodiment, the narrow channel includes a mask (not shown) positioned in front of the detector to increase optical separation between the physically separated detection elements. The narrow channel may be configured in the manners described above as described further herein.

As described above, the narrow channel may include collector 74 configured to collect the light scattered from the different portions of the spot. In one embodiment, the narrow channel includes detector 78 configured to separately and simultaneously detect the collected light scattered from the different portions of the spot and another detector (not shown) configured to separately and simultaneously detect the collected light scattered from the different portions of the spot. In one such embodiment, the two detectors are positioned such that there is a half pixel shift between the two detectors. In addition, the narrow channel may be configured such that the different output separately generated by the second detection subsystem is substantially unaffected by movement of the wafer in a direction substantially perpendicular to the surface of the wafer being inspected. Each of the embodiments of the narrow channel described above may be further configured as described herein.

The system embodiments described herein preferably include the first detection subsystem and at least one of the side detection subsystems described above. The system embodiments described herein may include any other detection subsystem(s) described herein in any combination. For example, the system may include all of the detection subsystems described herein. In this manner, the signals from all of the detection subsystems (e.g., the first detection subsystem, the two side detection subsystems, and the narrow channel, which may or may not be configured to simulate multi-spot inspection) may be present at the same time. It is possible, therefore, to combine the signals in any way that is considered advantageous. For example, the computer subsystem may be configured to perform one or more inspection-type functions (e.g., defect detection, defect classification, etc.) using some combination of the output generated by the first detection subsystem, the two side detection subsystems, and the narrow channel. In another example, as described further herein, the system may include two imaging collectors and one or two non-imaging collectors. However, the system may include any (reasonable) number of both types of collectors. For example, as described above, the non-imaging collectors may include the collectors in the wide and narrow channels of the system. However, these non-imaging collectors may be broken up or segmented into smaller collectors to optimize the capture of various defect types.

It is noted that the figures are provided herein to generally illustrate different configurations for the system embodiments described herein. Obviously, the system configurations described herein may be altered to optimize the performance of the system as is normally performed when designing a commercial system. In addition, the systems described herein may be implemented using an existing inspection system (e.g., by modifying an existing inspection system based on the embodiments described herein) to such as the SPx series of tools. For example, the basic structure of the system embodiments described herein is that of the SPx (e.g., SP1, SP2, etc.) series of tools with modifications described herein (e.g., adding one or more of the side collectors described herein, segmenting the narrow channel as described herein, modifying the computer subsystem such that it can perform the functions described herein, etc.). For some such systems, the functionality of the system embodiments described herein may be provided as optional functionality of the system (e.g., in addition to other functionality of the system). In this manner, the embodiments described herein may be used to provide enhanced defect detection sensitivity in the SPx family of products. For example, the embodiments described herein may be used to provide a sensitivity enhancement in detecting relatively small defects on both smooth and rough surfaces in the SPx family of products. In this manner, the embodiments described herein may be used to extend the capabilities of the SPx systems to the next level. For example, although the SPx systems are the benchmark in sensitivity in the inspection of unpatterned wafers, the embodiments described herein can assure the extensibility of the systems through enhancements that maintain the main characteristics of the system and are, at the same time, not inordinately difficult to implement. Alternatively, the systems described herein may be designed "from scratch" to provide completely new systems.

In some embodiments, the systems described herein may be configured as a "stand alone tool" or a tool that is not physically coupled to a process tool. However, such a system may be coupled to the process tool by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a "cluster tool," or a number of process modules coupled by a common handler.

Each of the embodiments of the system described above may be further configured according to any other embodiment(s) described herein.

As described above, the illumination subsystem may be configured to direct the light from the light source to the spot on the wafer at a substantially normal angle of incidence. Accordingly, another embodiment of a system configured to inspect a wafer includes an illumination subsystem configured to direct light to a spot on the wafer at a substantially normal angle of incidence. The substantially normal angle of incidence may or may not be exactly normal to the upper surface of the wafer. For example, a substantially normal angle of incidence may be an angle of incidence that is within about 2 degrees to about 5 degrees of exactly normal to the upper surface of the wafer. In this manner, the illumination subsystem may be configured in this embodiment to illuminate the wafer with normal or near normal incidence illumination. Such an illumination subsystem may be further configured as described herein.

The embodiment of the system also includes a first detection subsystem configured to detect light scattered from one portion of the spot on the wafer and to generate output responsive to the detected light. The first detection subsystem may be configured in this manner as described herein and may be further configured as described herein. In addition, the system includes a second detection subsystem configured to separately and simultaneously detect light scattered from different portions of the spot on the wafer and to separately generate different output responsive to the separately detected light. The entire collection space of the second detection subsystem spans only a portion of azimuthal angles at which the first detection subsystem detects the scattered light. The second detection subsystem may be configured in this manner as described herein and may be further configured as described herein.

This embodiment of the system further includes a computer subsystem configured to detect defects on the wafer using the output generated by the first detection subsystem and the different output separately generated by the second detection subsystem. The computer subsystem may be configured in this manner as described herein and may be further configured as described herein. This embodiment of the system may be further configured according to any other embodiments described herein. In addition, this embodiment of the system may be configured as shown in any of the figure(s) described herein.

An additional embodiment relates to a method for inspecting a wafer. The method includes directing light to a spot on the wafer at an oblique, or normal, angle of incidence. Directing the light to the spot on the wafer may be performed as described herein using any of the illumination subsystem embodiments described herein. The spot on the wafer may be configured as described herein. In addition, the oblique angle of incidence may include any of the oblique angles of incidence described herein.

The method also includes detecting light scattered from one portion of the spot on the wafer and generating first output responsive to the detected light scattered from the one portion. Detecting the light scattered from the one portion of the spot and generating the first output may be performed as described herein using any of the first detection subsystem embodiments described herein and/or the narrow channel embodiments described herein. The one portion of the spot may be configured as described herein. The first output may include any of the output described herein.

In addition, the method includes separately and simultaneously detecting light scattered from different portions of the spot on the wafer and separately generating different output responsive to the separately detected light. Separately and simultaneously detecting the light scattered from the different portions and separately generating the different output may be performed as described herein using any of the second and/or third detection subsystem embodiments configured as described herein in this manner. The different portions of the spot may be configured as described herein. The separately generated different output may include any such output described herein.

The light scattered from the different portions is detected at only a portion of the azimuthal angles at which the light scattered from the one portion is detected. The portion of the azimuthal angles at which the light scattered from the different portions is detected may include any such azimuthal angles described herein, and the azimuthal angles at which the light scattered from the one portion is detected may include any such azimuthal angles described herein.

The method further includes detecting defects on the wafer using the first output and the separately generated different output. Detecting the defects on the wafer using the first output and the separately generated different output may be performed as described herein using any of the embodiments of the computer subsystem described herein.

The method described above may include any other step(s) described herein. For example, the method described above may include any of the step(s) that can be performed by any of the system(s) described herein. In addition, the method described above may be performed by any of the system embodiments described herein and shown in the figures.

Information about the defects detected by the embodiments described herein may be used to alter a parameter of a process or a process tool using a feedback control technique, a feedforward control technique, or an in situ control technique. The parameter of the process or the process tool may be altered automatically.

The embodiments described herein may also include or be configured for storing results of one or more steps of one or more methods or produced by the computer subsystem described herein in a storage medium. The results may include any of the results described herein. The results may be stored in any manner known in the art. The storage medium may include any suitable storage medium known in the art. After the results have been stored, the results can be accessed in the storage medium and used by any of the method or system embodiments described herein, any other method, or any other system. Furthermore, the results may be stored "permanently," "semi-permanently," temporarily, or for some period of time. For example, the storage medium may be random access memory (RAM), and the results may not necessarily persist indefinitely in the storage medium.

Further modifications and alternative embodiments of various aspects of the invention may be apparent to those skilled in the art in view of this description. For example, systems and methods for inspecting wafers are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a wafer, comprising:
   an illumination subsystem configured to direct light to a spot on the wafer at an oblique angle of incidence;
   a first detection subsystem configured to detect light scattered from one portion of the spot on the wafer and to generate output responsive to the detected light;
   a second detection subsystem configured to separately and simultaneously detect light scattered from different portions of the spot on the wafer and to separately generate different output responsive to the separately detected light, wherein the entire collection space of the second detection subsystem spans only a portion of azimuthal angles at which the first detection subsystem detects the scattered light, wherein the second detection subsystem comprises a first detector configured to separately and simultaneously detect the light scattered from the different portions of the spot and a second detector configured to separately and simultaneously detect the light scattered from the different portions of the spot, and wherein the first and second detectors are positioned such that there is a half pixel shift between the first and second detectors; and a computer subsystem configured to detect defects on the wafer using the output generated by the first detection subsystem and the different output separately generated by the second detection subsystem.

2. The system of claim 1, wherein the one portion of the spot has an area on the wafer that is approximately equal to the entire area of the spot on the wafer.

3. The system of claim 1, wherein an area of the one portion of the spot is larger than an area of each of the different portions of the spot.

4. The system of claim 1, wherein none of the different portions within the spot overlap any other of the different portions within the spot.

5. The system of claim 1, wherein the different portions in combination extend across an area within the spot that is smaller than the entire area of the spot.

6. The system of claim 1, wherein the first detection subsystem comprises an ellipsoidal collector configured to collect the light scattered from the one portion of the spot on the wafer.

7. The system of claim 1, wherein the second detection subsystem is further configured to detect the light scattered from the different portions at one or more polar angles that are closer to the wafer than polar angles at which the first detection subsystem detects the scattered light.

8. The system of claim 1, wherein the second detection subsystem is further configured to preserve information about the different portion of the spot from which the separately detected light was scattered and to not preserve information about polar and azimuthal angles within the entire collection space of the second detection subsystem at which the light was scattered from the different portions of the spot.

9. The system of claim 1, wherein the second detection subsystem further comprises a collector configured to collect the light scattered from the different portions of the spot.

10. The system of claim 1, wherein the first detector comprises a multi-anode photomultiplier tube.

11. The system of claim 1, wherein the first detector comprises physically separated detection elements, and wherein the second detection subsystem further comprises a mask positioned in front of the first detector to increase optical separation between the physically separated detection elements.

12. The system of claim 1, wherein the second detection subsystem further comprises optical fibers configured to separately and simultaneously direct the light scattered from the different portions to different detection elements such that the different detection elements separately and simultaneously detect the light scattered from the different portions of the spot, and wherein the second detection subsystem further comprises micro-lenses positioned in front of the optical fibers and configured to eliminate dead spaces between adjacent optical fibers.

13. The system of claim 1, wherein the second detection subsystem is further configured such that the different output separately generated by the second detection subsystem is substantially unaffected by movement of the wafer in a direction substantially perpendicular to a surface of the wafer being inspected.

14. The system of claim 1, wherein the illumination subsystem is further configured to direct the light to the spot on the wafer at the oblique angle of incidence and a first azimuthal angle, wherein the second detection subsystem is further configured to separately and simultaneously detect the light scattered from the different portions of the spot at one or more azimuthal angles different than the first azimuthal angle, and wherein the first azimuthal angle and the one or more azimuthal angles are not opposite to each other.

15. The system of claim 1, further comprising a third detection subsystem configured to separately and simultaneously detect light scattered from the different portions of the spot on the wafer and to separately generate different output responsive to the scattered light separately detected by the third detection subsystem, wherein the second and third detection subsystems collect and detect the scattered light at different azimuthal angles.

16. The system of claim 1, further comprising a third detection subsystem configured to detect light scattered from the one portion of the spot on the wafer and to generate output responsive to the scattered light detected by the third detection subsystem, wherein the third detection subsystem comprises a refractive collector positioned such that an optical axis of the refractive collector is substantially perpendicular to a surface of the wafer being inspected.

17. The system of claim 1, further comprising a third detection subsystem configured to separately and simultaneously detect light scattered from the different portions of the spot on the wafer and to separately generate different output responsive to the scattered light separately detected by the third detection subsystem, wherein the third detection subsystem comprises a refractive collector positioned such that an optical axis of the refractive collector is substantially perpendicular to a surface of the wafer being inspected.

18. The system of claim 1, wherein the computer subsystem is further configured to perform a convolution on the different output separately generated by the second detection subsystem and to detect the defects on the wafer using results of the convolution.

19. The system of claim 1, further comprising a stage configured to rotate and translate the wafer while the light is directed to the spot on the wafer by the illumination subsystem such that the light directed to the spot is scanned across the wafer.

20. A method for inspecting a wafer, comprising:

directing light to a spot on the wafer at an oblique angle of incidence;

detecting light scattered from one portion of the spot on the wafer and generating first output responsive to the detected light scattered from the one portion;

separately and simultaneously detecting light scattered from different portions of the spot on the wafer and separately generating different output responsive to the separately detected light using a detection subsystem, wherein the light scattered from the different portions is detected at only a portion of the azimuthal angles at which the light scattered from the one portion is detected, wherein the detection subsystem comprises a first detector configured to separately and simultaneously detect the light scattered from the different portions of the spot and a second detector configured to separately and simultaneously detect the light scattered from the different portions of the spot, and wherein the first and second detectors are positioned such that there is a half pixel shift between the first and second detectors; and detecting defects on the wafer using the first output and the separately generated different output.

21. A system configured to inspect a wafer, comprising:

an illumination subsystem configured to direct light to a spot on the wafer at a substantially normal angle of incidence;

a first detection subsystem configured to detect light scattered from one portion of the spot on the wafer and to generate output responsive to the detected light;

a second detection subsystem configured to separately and simultaneously detect light scattered from different portions of the spot on the wafer and to separately generate different output responsive to the separately detected light, wherein the entire collection space of the second detection subsystem spans only a portion of azimuthal angles at which the first detection subsystem detects the scattered light, wherein the second detection subsystem comprises a first detector configured to separately and simultaneously detect the light scattered from the different portions of the spot and a second detector configured to separately and simultaneously detect the light scattered from the different portions of the spot, and wherein the first and second detectors are positioned such that there is a half pixel shift between the first and second detectors; and a computer subsystem configured to detect defects on the wafer using the output generated by the first detection subsystem and the different output separately generated by the second detection subsystem.

* * * * *